United States Patent [19]
Edelson

[11] 4,321,919
[45] Mar. 30, 1982

[54] METHOD AND SYSTEM FOR EXTERNALLY TREATING HUMAN BLOOD

[75] Inventor: Richard L. Edelson, Roseland, N.J.

[73] Assignee: Leukocyte Research, Inc., Detroit, Mich.

[21] Appl. No.: 102,553

[22] Filed: Dec. 11, 1979

[51] Int. Cl.³ ............................................... A61M 1/03
[52] U.S. Cl. ................................ 128/214 R; 128/395; 422/44; 128/1 R; 128/DIG. 3
[58] Field of Search ............ 128/214 B, 275.1, 207.22, 128/214 R, 214.2, 1.1, 1 R, 395, DIG. 3

[56] References Cited

U.S. PATENT DOCUMENTS 1,683,877  9/1928  Edblom et al. ...................... 128/395
3,788,319  1/1974  Gillette ............................ 128/214 B

OTHER PUBLICATIONS

Bordin, Fand Baccichetti, Furocoumarin Photosensitive Effect on Virus-Producing Graffi Leukemia Cells, 1974.
Psoralen Photosensitization of LI210 Leukemia Cells . . . Carlasse, F. et al, 2, Naturforsch, 33c, 92–95, 1978.
Sunlight and Man, Chapt. 22, Fitzpatrick (ed), U. of Tokyo Press, 1974.

Primary Examiner—Robert W. Michell
Assistant Examiner—Nancy A. B. Swisher

[57] ABSTRACT

A method and system are disclosed for externally treating human blood, with the objective of reducing the functioning lymphocyte population in the blood system of a human subject. According to the method, blood is withdrawn from the subject and passed through an ultraviolet radiation field in the presence of from about 1 nanogram to 100 micrograms per ml of blood, of a dissolved psoralen capable of forming photoadducts with DNA, to thereby effect covalent bonding between the psoralen and the nucleic acid of the lymphocytes, thereby altering the said nucleic acid and inhibiting the metabolic processes of the lymphocytes; and thereupon returning the irradiated blood to the subject. The withdrawn blood may be formed into an extracorporeal stream and flowed through a treatment station whereat the irradiation is effected, as for example by exposure to UV energy in the wave length range of from about 3200 to 4000 Angstroms; and such flow process may be conducted on a continuous basis. If desired, at least portions of the treated blood may then be separated, as for example by a continuous centrifuge, before returning the remaining diverted blood to the subject.

16 Claims, 5 Drawing Figures

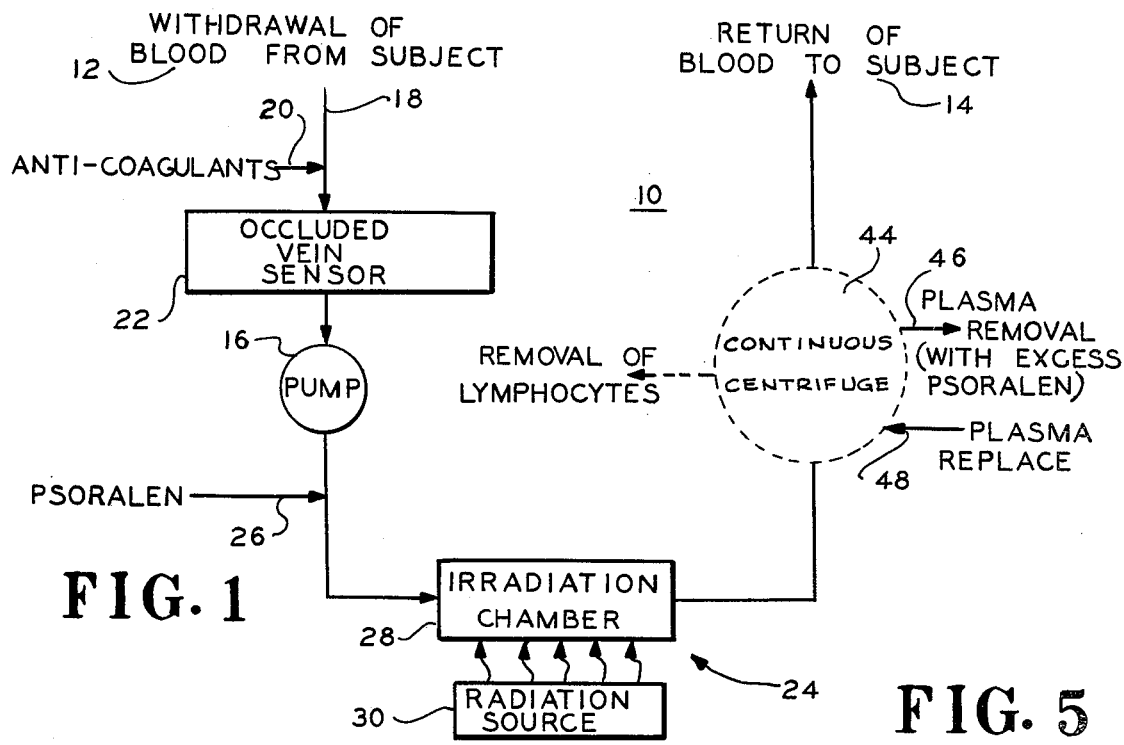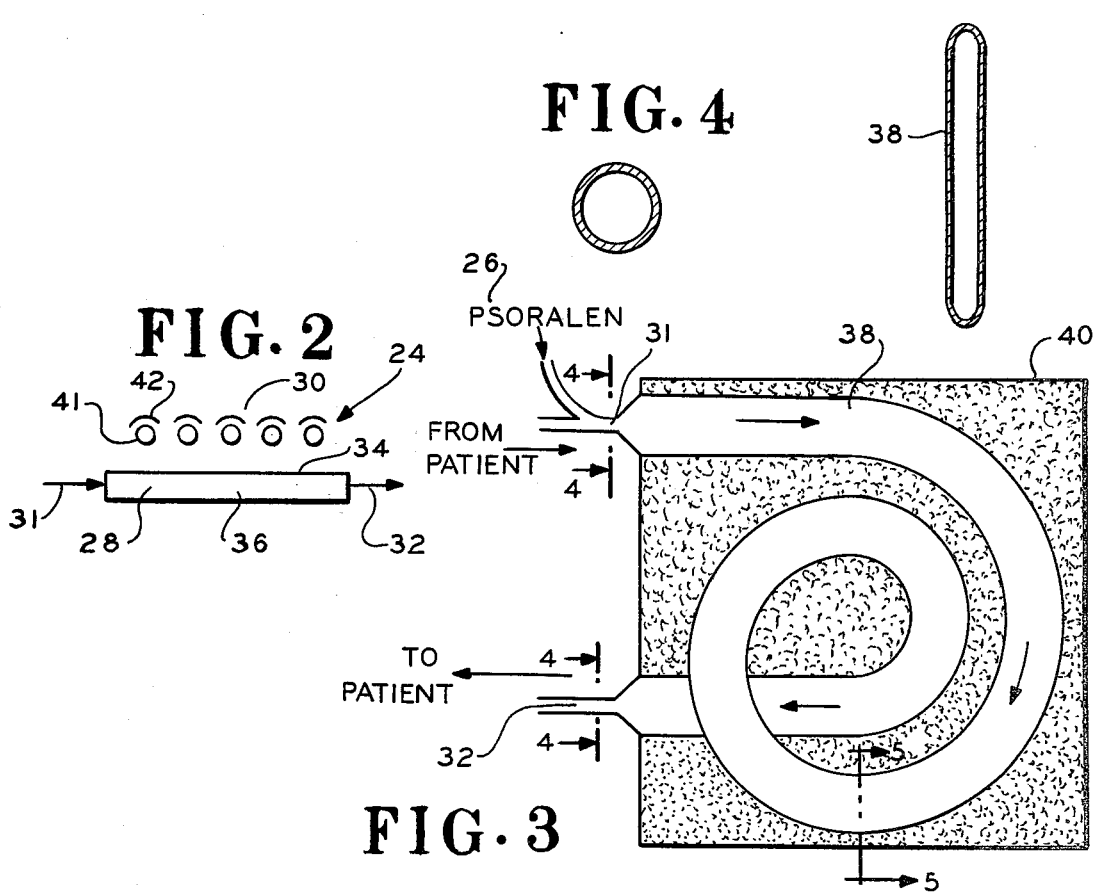

METHOD AND SYSTEM FOR EXTERNALLY TREATING HUMAN BLOOD

BACKGROUND OF INVENTION

This invention relates generally to methods and systems for medical treatment of the human body, and more specifically relates to a method and system usable in treating the blood supply of a human subject for the purpose of reducing the functioning lymphocyte population in the blood supply of such subject.

In a number of highly significant human diseases, including certain forms of leukemia, the population of certain types of leucocytes, including especially lymphocytes, increases inordinately in comparison to the other populations of nucleated cells in normal blood. While the excessive population of such lymphocytes represents a result of, rather than the underlying cause of the disease, the excessive lymphocyte population brings direct adverse effects to the patient if steps are not taken to reduce same. Complications thus rapidly develop which impair function of bodily organs, and eventually a life-threatening situation is presented.

It should also be appreciated that excessive increase in the lymphocyte population of the blood supply can occur in other human maladies, in addition to lymphocytic leukemias. Thus, for example, such results can obtain in consequence of severe allergic reactions to administered agents, including drugs or the like, or in many other lymphocyte-mediated diseases.

In addition to the development over the years of pharmaceutical agents and the like, which may non-specifically reduce the lymphocyte population, e.g. by altering the underlying production rate of same, various techniques have from time to time been used in an effort to directly attack the problem, as for example by mechanically removing such lymphocytes from the blood supply. It is thus known, for example, to pass the blood supply through a continuous centrifuge, whereat one seeks to selectively remove lymphocytes to reduce the population of the latter in the thereby processed blood supply. In general, however, this method tends to be very inefficient, in part because the density differences between the blood fractions including the undesired lymphocytes and fractions which include desired blood components, is insufficient to assure that high percentages of the former are removed while retaining high proportions of the latter.

It is also well-known to treat diseases such as leukemia with high energy electromagnetic radiation, including in the X-ray region. While such treatment is often directed at internal bodily organs whereat the blood cells are being generated, it has also been known to irradiate the blood supply with x-radiation at a point external to the body (the blood having first been withdrawn), whereby the radiation is not rendered directly incident on the body or internal organs of same. This method, while powerful, is indiscriminate, in that the intensely disruptive energy, in addition to destroying undesirable cells, disables or destroys components of the blood which are desired to be retained in vital status.

For many years, it has been known that certain heterocyclic furocoumarins possess photoactive properties that render same useful in the treatment of certain human diseases. A noteworthy example of this occurs in certain recently reported methods for treatment of psoriasis.

The photoactive compounds referred to are all members of a group of coumarin derivatives which are commonly referred to as "psoralens", the basic member of which is the (photoactive) compound psoralen, having the structure:

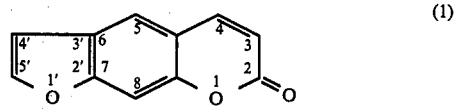

The remaining compounds of interest for this invention (as will be discussed in greater detail hereinbelow) are all derivatives of psoralen, i.e. of structure (1). In accordance, however, with accepted terminology in the nomenclature of the pertinent chemical art, the phrase "psoralen" or "a psoralen" will be used at places in this specification to refer to certain derivatives of structure (1) which include "psoralen" in their accepted name, such as 8-methoxypsoralen, 5-methoxypsoralen, etc.

In an article appearing in the *New England Journal of Medicine*, Volume 291, No. 23 for Dec. 5, 1974, John A. Parrish, M.D. et al, thus report a method involving oral administration of 8-methoxypsoralen (8-MOP) to a patient who is thereafter treated by exposure to a high intensity longwavelength ultraviolet light source, i.e. to a source of ultraviolet radiation in the UVA wavelength region, and preferably in the wavelength range between about 3200 and 4000 Angstroms, with a peak emission at about 3650 Angstroms. The highly successful treatment is deemed to be effective by interrupting the disease process in psoriasis, a disorder characterized by an accelerated cell cycle and rate of DNA synthesis. The treatment acts to inhibit DNA synthesis by formation of C-4 cyclo-addition products between the pyrimidine bases of the nucleic acids and psoralen molecule. Since the 5,6 double bond of the pyrimidine can photoreact with the psoralen molecule at either the 3,4 double bond of the pyrone ring or at the 4',5' double bond of the furan ring, two types of photoadducts are possible. In consequence formation of photo-induced DNA cross-links is enabled.

In this sequence of treatment thus employed in the treatment of psoriasis, it has been common to place the patient following administration of the psoralen, in a light box or other environment whereat the high intensity illumination is effected. It has come to the attention of investigators that a side effect resulting from the cited treatment, can occasionally be the destruction of certain nucleated blood cells. Investigation appears to establish that such result obtains because the incident UV radiation has sufficient penetrating power, to induce some bonding between the psoralen introduced into the bloodstream and the nucleic acid of the nucleated blood cells such as the lymphocytes. In consequence the metabolic processes of such modified lymphocytes are detrimentally affected, eventually leading to the inactivation and ultimate destruction of same. This type of phenomenon has been studied in vitro, and among other places, is reported in an article by G. Lischka et al appearing in *Archives for Dermatological Research*, 259, 293-298 (1977). Of interest for present purposes is that the reported phenomenon is regarded as an undesirable side effect, which is incident to the beneficial results otherwise achieved during treatment of psoriasis.

SUMMARY OF INVENTION

Now, in accordance with the present invention, a method and system has been found which enables safe and effective reduction of the functioning lymphocyte population in the blood supply of a human subject. According to the method of invention, blood requiring such treatment, is withdrawn from the subject and irradiated with UVA radiation in a preferred wavelength range of from about 3200 to 4000 Angstroms, in the presence of from about 1 nanogram to 100 microgram per ml of blood of a dissolved psoralen of the type capable of forming photoadducts with DNA, to thereby effect covalent bonding between the psoralen and the nucleic acid of the lymphocytes present in the blood. The said nucleic acid is thereby altered to inhibit the metabolic processes of the said lymphocytes, after which the irradiated blood is returned to the human subject.

The withdrawn blood can be treated in batch, but preferably is formed into an extracorporeal stream and passed through a treatment station whereat the irradiation is effected. Such treatment station may take the form of an extended flattened tubular passageway, the walls of which are substantially transparent to the incident long-wave UV energy (UVA) used to activate the psoralen. Typical radiation doses range from about 0.1 to 100 joules per $cm^2$ of blood surface where the process is carried out on a continuous or discontinuous basis, and typical flow rates through the irradiation station can be in the range of from about 10 to 75 ml/min.

Following treatment, the entire batch, or irradiated flow of diverted blood, can be returned to the patient with all blood components intact. The lymphocytes, however, by virtue of the treatment, have been so altered that their metabolic functioning is rapidly impaired, and especially the ability of same to divide, in consequence of which destruction of the impaired lymphocytes rapidly occurs. Moreover, the impairment and destruction tends to be selective in certain diseases such as leukemia, to the cells most sought to be reduced, by virtue of the fact that it is such cells which are undergoing the most intense metabolic activities to begin with, whereby they are the cells most subject to disablement by the present process.

A preferred psoralen for use in the process of the present invention is 8-methyoxypsoralen (8-MOP, also known as methoxsalen). Other photoactive psoralens useful in practice of the present invention include psoralen itself, i.e. structure (1), and 4,5',8-trimethylpsoralen. Less preferred, but still useful photoactive psoralens for use in the invention include 5-methoxypsoralen, 4-methylpsoralen, 4,4-dimethylpsoralen, 4,5'-dimethylpsoralen, and 4',8-dimethylpsoralen.

Further discussion of these photoactive psoralens may be found in the tutorial article entitled *Photobiology and Photochemistry of Furocoumarins (Psoralens)* by M. A. Pathak et al, which article appears as Chapter 22 of the work *Sunlight and Man*, edited by Thomas B. Fitzpatrick et al, University of Tokyo Press (1974). This article observes (which is appropriate for present purposes) that the most effective photoactive psoralens include the compound psoralen proper, i.e. structure (1), and derivatives of structure (1) wherein methyl or methoxy groups are substituted at one or more of the 4,4',5' and 8 positions, as for example in the aforementioned 8-MOP, which has the structure:

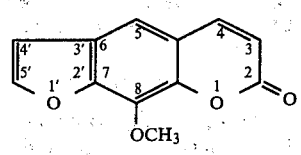

and 4,5',8-trimethylpsoralen, which has the structure:

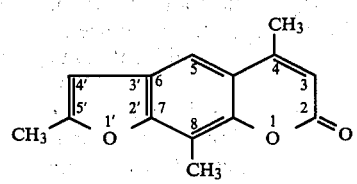

As aforementioned, the reactive sites of the nucleic acids are considered to be the pyrimidine bases, and it is believed that the photoinduced reaction of the present invention involves the activated psoralen and one or more of the pyrimidine bases normally present in nucleic acids, such as thymine, cytosine, uracil or so forth. A C4 cyclo-addition takes place; the pyrimidine bases always react with their 5,6 double bond, while the psoralens can react with either their 3,4 double bond or with their 4',5' double bond. In consequence two types of photo-adducts can be obtained. This ability to bond at two regions of the linear psoralen structure enables the said structure upon photo-activation to link to one pyrimidine base, or to two pyrimidine bases which engage both of the reactive double bonds of the psoralen structure. Where this double linking occurs, cross-linking can be effected between the two strands of DNA, which is particularly effective in inhibiting the metabolic functions of the associated nucleated cells, such as the lymphocytes.

BRIEF DESCRIPTION OF DRAWINGS

The invention is diagrammatically illustrated, by way of example, in the drawings appended hereto, in which:

FIG. 1 is a schematic flow diagram illustrating a preferred embodiment of a system operating in accordance with the present invention;

FIG. 2 is a schematic elevational view of the irradiation station portion of the FIG. 1 system;

FIG. 3 is a plan view, schematic in nature, of one embodiment of the irradiation station of FIG. 2; and FIGS. 4 and 5 are cross-sectional views, taken along the lines 4—4 and 5—5 of FIG. 3, and illustrate the configurations of the flow passageway and the output passage for the FIG. 3 device.

DESCRIPTION OF PREFERRED EMBODIMENT

In FIG. 1 herein a schematic diagram appears of a system 10 in accordance with the present invention. Except for the irradiation station, the bulk of the components of system 10 are per se conventional and known in the art; and hence it is not deemed appropriate or necessary to vastly detail same.

As indicated in the Figure, blood may initially be withdrawn from the human subject, as at 12. Typically the blood is withdrawn via a donor needle, which may e.g. be emplaced at the right antecubital vein. In the showing of FIG. 1, it is assumed that the processing of blood pursuant to the invention is conducted on a continuous basis, i,e. for purposes of the present discussion the flow may be regarded as continuous from withdrawal at 12, to final return of the blood to the subject at 14. Such return 14 is typically effected via a recipient needle positioned in the left antecubital vein. Where the flow is indeed continuous in this manner, a typical blood flow utilizable in practice of the invention is in range of from about 10 to 75 ml/min, with a more preferred range being from about 40 to 50 ml/min. The indicated flow rates are effected by means of a pump 16, which is positioned in the extracorporeal blood flow stream generally indicated at 18, and may comprise one of numerous types of pumps used for blood flow treatment purposes, including such pumps as those available from Haemonetics Corp. under Model Designation 30.

As is known in the pertinent medical art, anti-coagulants are preferably injected into the extracorporeal blood flow stream at 20, i.e. close to the point of blood withdrawal. Such anti-coagulants can comprise solutions of acid citrate dextrose and/or of heparin, or of other known compositions useful for this purpose.

An occluded vein sensor 22 is preferably provided in stream 18 for purposes, as known in the art. Such sensor basically comprises a reservoir or buffer volume, the object of which is to prevent or inhibit generation or continued existence of bubbles in the blood flow stream.

Pursuant to a preferred mode of practicing the present invention, the photoactive psoralen is preferably added to the blood of the human subject external to such subject; and thus as shown in the system 10 of FIG. 1, may be provided to the flowing blood downstream of pump 16, and just upstream of where the blood enters the irradiation station 24.

As has been discussed under the "Summary of Invention" the preferred psoralen for use in the process of the invention is 8-methoxypsoralen (8-MOP). As also discussed, other photoactive psoralens as previously described, are also utilizable in the method of the invention. The basic technique used in introducing the psoralen, is to disolve same in an isotonic solution, which thereafter is directly injected into the flowing blood stream, as at 26. The psoralen is injected at a rate in comparison to the blood flow rate, as to achieve a concentration in the blood thereafter passed to irradiation station 24, of from about 1 nanogram to 100 micrograms of dissolved psoralen per ml of blood.

In the foregoing connection it should be appreciated that the primary objective of the operations thus far described is one of achieving the desired dissolved concentration of the photoactive psoralen prior to introduction of the blood to the irradiation station. In accordance with a further aspect of the invention, it will therefore be appreciated that the said photoactive compound need not necessarily be directly introduced by injection into the extracorporeal blood stream 18 flowing in FIG. 1. Rather, it is also acceptable to achieve the desired psoralen concentration levels by orally or otherwise administering the compound directly to the patient.

Indeed, in those instances of the prior art which have been heretofore discussed, wherein 8-MOP has been utilized in treatment of psoriasis, it has been usual for the psoralen to be orally administered. Where, pursuant to the invention, the psoralen is thus orally administered, it can be provided in oral dosages of from about 0.6 to 1.0 mg per kg of body weight. The desired concentration range in the blood used for practice of the invention, is then achieved in about two hours from oral administration.

However, it is preferred to introduce the psoralen to the extracorporeal stream (or to an extracorporeal batch volume) in order to achieve more exact concentration levels; and further, to avoid or minimize possible side effects and the like, which can occur from administration of any drug directly to the body system.

At irradiation station 24, consisting of an irradiation chamber 28 and radiation source 30, the blood now carrying in solution the desired psoralen concentration, is subjected to ultraviolet radiation in the UVA portion of the spectrum. Such UVA portion of the spectrum includes primarily wave lengths in the range from about 3200 to 4600 Angstroms. For present purposes it is preferred to use a radiation source having the bulk of its spectral components in the 3200 to 4000 Angstrom range, with peak intensities at about 3600 to 3700 Angstroms. Such radiation passes readily through conventional clear plastic tubing.

In FIG. 2, a schematic elevational view appears of an irradiation station 24 of a type suitable for use with the invention. Such station consists of a blood treatment or irradiation chamber 28, having an inlet 31 and an outlet 32, enabling blood flow through the chamber, and a spaced source 30 of UVA radiation. The chamber 28 can take various forms, with the principal requirement for same being that the wall 34 of same opposed to source 30, be substantially transparent to the incident UVA radiation. The said chamber (or at least wall 34) can therefore typically be comprised of various substantially UVA-transparent plastics, as are commonly used in tubing constructed for administration of standard intravenous solutions, such as polyvinyl chloride and the like.

In one embodiment of chamber 28, the said device can comprise a simple envelope, i.e., the central void 36 is substantially of thin rectangular cross-section. Where, however, the blood is to be treated as preferred, on a continuous basis, superior flow characteristics and better control of the exposure time can be achieved where blood treatment chamber 28 has a configuration as shown in FIGS. 3, 4 and 5. In this instance a tubular coil 38, which in cross-section (FIG. 5) is flattened to a very elongated elipse, is fixedly maintained in or upon a support plate 40. The blood flow inlet 30 to the coil is of circular cross section, and in terms of FIG. 1 is at a point downstream of pump 16. The feed-in for the psoralen compound is schematically depicted at 26. The highly flattened cross-section of the coil enables good flow for the blood passing through the coil, but, more importantly, enables good exposure of the flowing blood to the incident UVA radiation. The outlet 32 is again returned to a circular cross-section.

UVA source 30 may comprise one or a plurality of side-by-side or otherwise arranged UVA light sources 41, each of which may be backed by a reflector 42. The UVA sources can comprise commercially available lamps, numerous types of which are known in the art.

By way of example, source 30 can comprise a single 1000 watt Hg lamp of the type available from Oriel Corporation of Stamford, Conn., under Model designation 6287. When used with appropriate filters this source provides a good relatively continuous spectrum of high intensity radiation between 3200 and 4000 Angstroms, with a peak emission at about 3650 Angstroms. The said lamp with a suitable reflector can be positioned approximately 5 to 30 cm from chamber 28. With the flow rates utilized in accordance with one aspect of the invention, such a source will provide absorbed energy in the flowing blood within the range of interest for practicing the method of the invention.

The blood flow from irradiation station 24 proceeding as shown in FIG. 1 via outlet 32, can be directly returned to the subject at 14. Under these circumstances, the modified lymphocyes, i.e. wherein bonding of nucleic acid to the photo-activated psoralen compounds has been effected, are impaired in their metabolic processes, in consequence of which the said lymphocytes will be rapidly broken down and destroyed by normal processes occurring in the subject. Since further, and as already discussed, the metabolic processes in the abnormal lymphocytes associated with disease conditions are usually accelerated, the breakdown in functioning, and the destruction of such abnormal lymphocytes, is accelerated beyond the corresponding effects on rate of normal lymphocytes, thereby contributing to the destruction of the abnormal lymphocyte population in the blood supply of the subject.

The burden placed upon the body's organ system, however, can be further alleviated, by utilizing in conjunction with the present system, a continuous centrifuge 44, which device serves several functions.

It is to be noted that continuous centrifuges of the type here utilized, have been long employed in blood flow processing systems commercially available from several manufacturers, including Haemonetics Corporation of Braintree, Mass., and the IBM Corporation, Medicals Products Division, of Monsey, N.Y. In the prior art systems in which such devices have been utilized all elements of FIG. 1 have been present, with the singularly important exception of the irradiation station 24. The function of the continuous centrifuge in such prior art systems has been one of separating excess lymphocytes or other blood components of interest. Where so used, a detriment of such system was the inefficiency of same, i.e. the centrifuging process can at best remove about 40 to 50% of the lymphocytes, and unfortunately also removes numerous components which are in fact desired to be retained.

In the system 10 of the present invention, two functions can be performed by the continuous centrifuge 44. One of these, is removal of lymphocytes, as previously discussed. Because the present invention, however, relies primarily on impairment of function of the lymphocytes to ultimately reduce the functioning population of same, the centrifuge 44 need not be relied upon to the extent that same has been in the aforementioned prior art arrangements. From a mechanical viewpoint, this implies that one need not work as close to the specific gravity interface between the lymphocyte fraction of the blood and the desirable fractions of the blood which one seeks to retain. Thus one can avoid undue separation of those desired fractions of the whole blood.

The continuous centrifuge 44, may further be utilized for an additional important purpose. In particular, some or virtually all of the blood plasma may be removed at 46 and replaced with fresh plasma at 48. This washing technique enables one to effectively withdraw the excess psoralen compounds which may be present in the blood plasma, replacing the plasma at 46 with psoralen-free isotonic fluid. Thus, when the blood is returned to the subject at 14, it is substantially free of any excess psoralens, i.e. other that those which have combined with the nucleic acid components of the lymphocytes in the manner desired.

It should also be reemphasized that while the preferred mode of practicing the present invention, as illustrated in FIG. 1, contemplates a continuous operation, the blood treatment pursuant to the invention can be effected by batched techniques. Thus for example a distinct, fixed quantity of blood may initially be withdrawn from the subject. Such quantity or batch, may already have present therein the desired quantities of disolved psoralen, i.e. by prior adminstration to the patient; or the said psoralen may be admixed externally with the withdrawn blood. The said blood batch bearing the psoralen may then be provided to an irradiation station, where the desired quantity of UVA energy is rendered incident upon same. During this process the batch of blood can be flowed through the station as previously discussed, or if the quantity of blood is appropriate and the blood treatment chamber 28 of appropriate dimensions, the batch can simply be treated under static conditions until the desired energy has been dissipated. Thereafter, the treated blood is taken from the irradiation station, and either centrifuged as above discussed, or directly returned to the subject.

While the present invention has been particularly described in terms of specific embodiments thereof, it will be understood in view of the present disclosure, that numerous variations upon the invention are now enabled to those skilled in the art, which variations yet reside within the scope of the present invention. Accordingly, the invention is to be broadly construed, and limited only by the scope and spirit of the claims now appended hereto.

I claim:

1. A method for reducing the population of lymphocytes with intense metabolic activity in the blood supply of a human subject, comprising the steps of:
   withdrawing whole blood from said subject, forming said whole blood into an extracorporeal stream, flowing said stream through a treatment station which comprises a thin chamber substantially transparent to UV radiation, irradiating said withdrawn whole blood in said treatment station with UV radiation in the presence of about 1 nanogram to 100 micrograms of a dissolved psoralen capable when activated by said UV radiation to effect chemical bonding between said psoralen and said lymphocytes, thereby selectively inhibiting the metabolic processes of said lymphocytes; and returning the irradiated whole blood to said subject.

2. A method in accordance with claim 1, wherein said psoralen comprises 8-MOP.

3. A method in accordance with claim 1, wherein said withdrawing of said whole blood, passage to such treatment station, and return of said whole blood to said subject, is carried out as a continuous operation.

4. A method in accordance with claim 3, wherein the flow rate of said extracorporeal bloodstream is in the range of from about 10 to 75 ml/min.

5. A method in accordance with claim 3, including the further step of separating at least portions of said lymphocyte population before returning said whole blood to said subject, by passing said bloodstream through a continuous flow centrifuge.

6. A method in accordance with claim 5, wherein excess quantities of said psoralen are removed from the extracorporeal stream by withdrawing blood plasma at said centrifuge and replacing same with fresh psoralen-free plasma.

7. A method in accordance with claim 1, including the further step of separating at least portions of said lymphocyte population before returning said whole blood to said subject.

8. A method in accordance with claim 1, wherein said whole blood is irradiated with photoenergy in the UVA wavelength range, and at a radiation dose level of from about 0.1 to 100 joules/cm$^2$.

9. A method in accordance with claim 1, wherein said psoralen is dissolved in said whole blood by mixing same with said whole blood subsequent to withdrawing the whole blood from said subject.

10. A method in accordance with claim 1, wherein said psoralen is dissolved in said whole blood by administering said psoralen orally to said subject.

11. A method in accordance with claim 1, wherein said psoralen is methyl or methoxy substituted.

12. A method in accordance with claim 11, wherein said psoralen is methyl-substituted at one or more of the 4, 4', 5' and 8 positions.

13. A method in accordance with claim 12, wherein said psoralen comprises 4, 5',8-trimethylpsoralen.

14. A method for reducing the population of lymphocytes with intense metabolic activity in the blood supply of a human subject, comprising the steps of:
withdrawing whole blood from said subject, forming said whole blood into an extracorporeal stream, flowing said stream through a treatment station which comprises a thin chamber substantially transparent to UV radiation, irradiating said withdrawn whole blood in said treatment station with UV radiation in the presence of an effective amount of 8-methoxypsoralen within the range of from about 1 nanogram to 100 micrograms per ml of blood capable when activated by said UV radiation to effect chemical bonding between said 8-methoxypsoralen and said lymphocytes, thereby selectively inhibiting the metabolic processes of said lymphocytes; and returning the irradiated whole blood to said subject, wherein said process is carried out continuously.

15. The process of claim 14 wherein said chamber is a UV-transparent plastic.

16. The process of claim 14 wherein the psoralen, is an isotonic solution, is introduced into the extracorporeal stream.

* * * * *